(12) United States Patent
Allen et al.

(10) Patent No.: US 7,628,507 B2
(45) Date of Patent: Dec. 8, 2009

(54) RADIANCE OUTPUT AND TEMPERATURE CONTROLLED LED RADIANCE SOURCE

(75) Inventors: David W. Allen, Gaithersburg, MD (US); Howard Yoon, N. Potomac, MD (US)

(73) Assignee: The United States of America as represented by the Secretary of Commerce, The National Institute of Standards and Technology, Washington, DC (US)

( * ) Notice: Subject to any disclaimer, the term of this patent is extended or adjusted under 35 U.S.C. 154(b) by 430 days.

(21) Appl. No.: 11/144,303

(22) Filed: Jun. 3, 2005

(65) Prior Publication Data

US 2005/0270776 A1    Dec. 8, 2005

Related U.S. Application Data

(60) Provisional application No. 60/577,282, filed on Jun. 4, 2004.

(51) Int. Cl.
*F21V 9/10* (2006.01)
*G01J 1/32* (2006.01)
*G01K 15/00* (2006.01)

(52) U.S. Cl. .................. 362/230; 362/294; 362/373; 315/151; 315/158; 250/205; 250/552; 250/553; 374/2

(58) Field of Classification Search ................. 362/230, 362/294, 373; 257/88; 315/151, 158, 159; 250/205, 552, 553; 374/2
See application file for complete search history.

(56) References Cited

U.S. PATENT DOCUMENTS

| | | | | |
|---|---|---|---|---|
| 4,654,521 A | * | 3/1987 | Stevens | 250/227.24 |
| 5,278,432 A | * | 1/1994 | Ignatius et al. | 257/88 |
| 6,179,465 B1 | * | 1/2001 | Yam | 374/2 |
| 6,435,691 B1 | * | 8/2002 | Macey et al. | 362/101 |
| 6,481,874 B2 | * | 11/2002 | Petroski | 362/373 |
| 6,674,060 B2 | * | 1/2004 | Antila | 250/205 |
| 6,864,513 B2 | * | 3/2005 | Lin et al. | 257/99 |
| 7,095,187 B2 | * | 8/2006 | Young | 315/360 |
| 7,108,413 B2 | * | 9/2006 | Kwong et al. | 362/583 |
| 2004/0120156 A1 | * | 6/2004 | Ryan | 362/373 |
| 2005/0174753 A1 | * | 8/2005 | Cao et al. | 362/106 |

* cited by examiner

*Primary Examiner*—Ismael Negron
(74) *Attorney, Agent, or Firm*—Butzel Long

(57) ABSTRACT

The LED-radiance source is a suitable replacement of lamp-based integrating sphere sources where they are used as stable and uniform radiance sources. The LED-based radiance source includes an array of LEDs having substantially similar radiance output wavelengths and a radiation detector such as a photodiode that detects and monitors radiation directed from the LEDs. Temperature of the LEDs can be controlled by feedback from a photodiode, thereby allowing for control and stabilization of temperature-dependent radiation output.

1 Claim, 3 Drawing Sheets

US 7,628,507 B2

RADIANCE OUTPUT AND TEMPERATURE CONTROLLED LED RADIANCE SOURCE

RELATED APPLICATIONS

This application is based upon U.S. Provisional Patent Application Ser. No. 60/577,282, filed Jun. 4, 2004 to which priority is claimed under 35 U.S.C. §120.

TECHNICAL FIELD

The present invention relates to radiance emitting sources which can be used for the calibration and characterization of radiation thermometers, night vision devices, environmental remote sensing systems, biological agent detection, and any radiometer which needs a stable radiance source. In particular, the present invention is directed to LED-based radiance sources that are compact and provide stable and uniform radiance.

BACKGROUND ART

Recent advances in manufacturing techniques for producing solid-state lighting have led to an increase in the selection of wavelength and radiation intensity of LEDs. LEDs have several advantages that distinguish them from over conventional light sources. LEDs have stable lifetimes in the thousands of hours. In addition, LEDs have narrow-band spectral distributions which eliminate the need of a filter which is required when other conventional light sources are used in certain applications. LEDs are mechanically robust and less sensitive to physical and mechanical stresses which might occur during handling and transport. Such advantages of LED sources have been recognized with the development of integrating sphere sources which use LEDs that have many different center wavelengths for illumination as disclosed, for example, by S. W. Brown et al. (*Development of a Tunable LED-Based Colorimetric Source*, Journal of Research of National Institute of Standards and Technology, 107, pp. 363-371 (2002)). The ability to control the optical power of individual LEDs has led to a spectrally tunable source with a high degree of temporal stability.

Radiation thermometers are typically constructed with narrow-band filters. Since LED-based sources can be constructed to have common center wavelengths, such LED-based sources can be used as monochromatic light sources. These monochromatic sources that are based upon LEDs can be used to determine the size-of-source effect (SSE) which are typically only occasionally performed to characterize radiation thermometers as discussed by G. Machin et al. (*A Comparative Study of Size-of-Source Effect Determination Techniques*, Proceedings of Tempmeko 2001, Berlin, 2002, pp. 155-160) and H. W. Yoon et al. (*Methods to Reduce the Size-of-Source Effect in Radiation Thermometers*, submitted to the Proceedings of Tempmeko 2004, Croatia).

The present invention provides compact radiance sources based upon the use of LEDs that are much easier to use than large integrating sphere sources for determining the SSE. Since SSE has been found to be dependent on the scattering properties of the objectives of radiation thermometers, the SSE should be measured prior to any critical temperature determination. The radiance sources of the present invention allow for easy measurement of SSE and thus improvements in critical temperature determinations.

In addition, the LED-based radiance sources of the present invention provide stable and uniform radiance that can be used for the calibration and characterization of radiation thermometers, night vision devices, environmental remote sensing systems, biological agent detection, and any radiometer which needs a stable radiance source. In general, the LED-based radiance source can be uses as a replacement for lamp-based integrating sphere sources.

DISCLOSURE OF THE INVENTION

According to various features, characteristics and embodiments of the present invention which will become apparent as the description thereof proceeds, the present invention provides an LED illuminated radiance source which includes:

a housing having first and second ends, an array of LEDs provided at the first end of the housing and arranged to direct radiation toward the second end of the housing; and a radiation detector coupled to the housing between the first and second ends for detecting radiation directed from the LEDs though the housing.

The present invention further provides a compact LED radiance source that includes:

a tubular housing having first and second ends;

a replaceable LED module that comprises a plurality of LEDs having substantially similar radiance output wavelengths; and a radiation detector coupled to the housing between the first and second ends for detecting radiation directed from the LEDs though the housing.

The present invention further provides a method of providing a stable, uniform source of radiation which comprises the steps of:

a) providing a plurality of LEDs having a common wavelength;

b) supplying current to the plurality of LEDs to cause the plurality of LEDs to emit radiation;

c) monitoring the radiation emitted from the plurality of LEDs; and d) using the monitored radiation in step c) to control at least one of the temperature of the plurality of LEDs and the current supplied to the plurality of LEDs.

BRIEF DESCRIPTION OF DRAWINGS

The present invention will be described with reference to the attached drawings which are given as non-limiting examples only, in which.

BEST MODE FOR CARRYING OUT THE INVENTION

Figure 1:
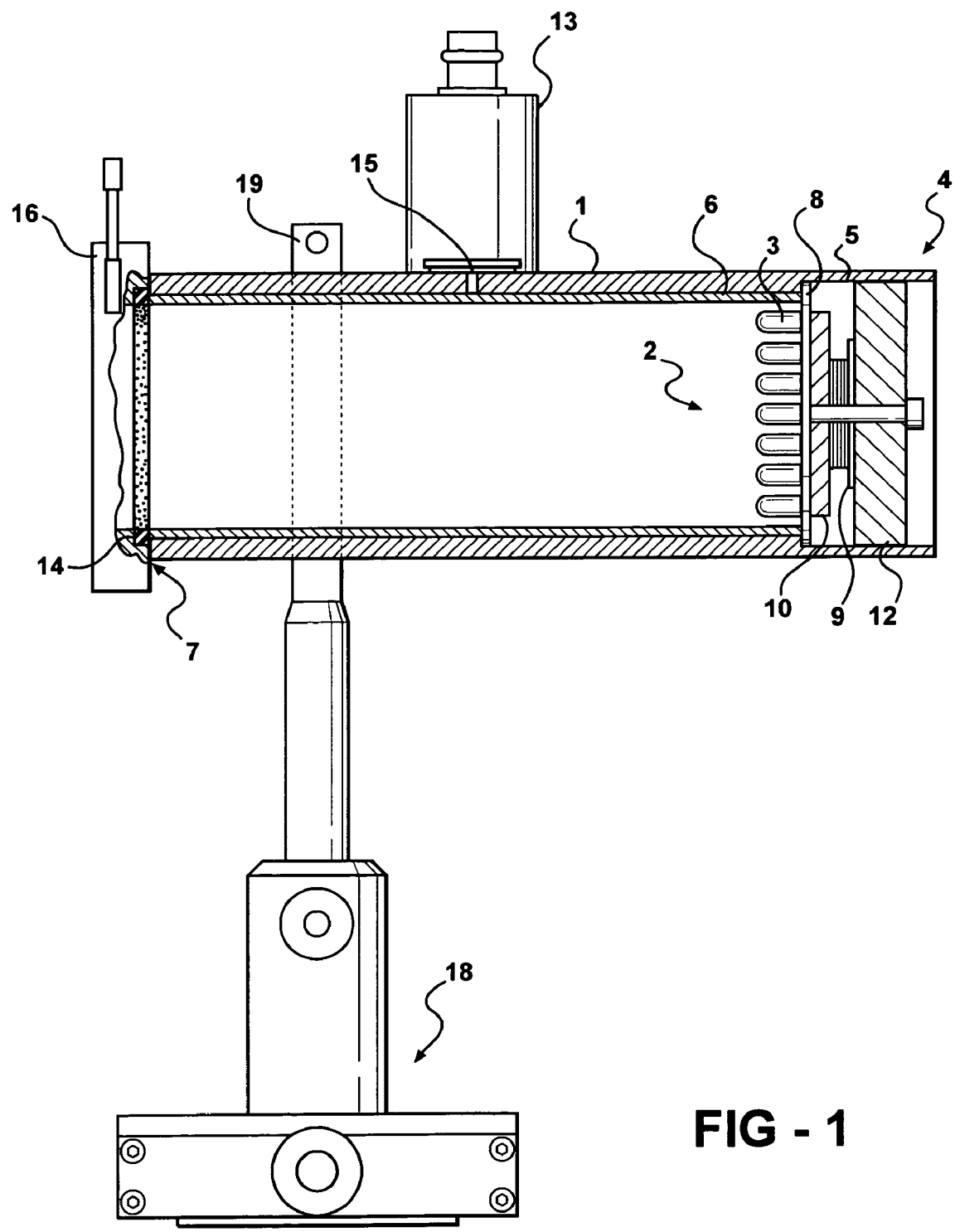
FIG. 1 is a cross-sectional side view of a LED Radiance Source (LRS) according to one embodiment of the present invention.

The present invention is directed to a portable radiance source that is based upon the use of LEDs. The LED radiance sources (LRSs) of the present invention are compact, temporally stable and uniform, making them particularly useful in applications such as calibration and characterization of radiation thermometers, night vision devices, environmental remote sensing systems, biological agent detection, and any radiometer which needs a stable radiance source. Other embodiments of the present invention can be based upon the use of laser diodes.

LEDs generally have stable lifetimes and are otherwise temporally stable. In order to compensate for any temporal instability of the LEDs used in the LED radiance sources of the present invention, provisions are made for monitoring radiance output of the LED radiance source that, according to one embodiment, uses a photodiode to monitor radiance output during use. Such monitoring is much more robust and accurate than a system that monitors and controls current supplied to radiation sources.

In addition to monitoring radiance output, the present invention provides for feedback control of the LED arrays. By monitoring the radiance output, the radiance can be controlled by using a feedback loop in conjunction with the source(s) that supply current to the LEDs. The temperature of the LEDs is monitored with a temperature sensor which can be used in conjunction with a cooling element and temperature controller. According to one embodiment, radiance output can be monitored and used to control the temperature of the LEDs so that temperature dependence of the radiation output can be controlled and/or stabilized.

The feedback control can be used to maintain the radiance level of the LED radiance sources relative to a standard (e.g., national or international) scale that can, for example, be maintained at a metrological institute (such as NIST). This would allow dissemination of the standard scale with all the advantages associated with the compact LED radiance sources of the present invention.

The LED radiance sources of the present invention include arrays of LEDs that are configured and provided in a housing so as to produce a spatially uniform radiance source. According to one embodiment, the LEDs can be arranged or provided in a circular configuration and used in a tubular housing in which case the resulting radiance will be spatially uniform near the central axis of the resulting LRS. Other configurations of the LEDs are possible and will result in different areas of spatial uniformity. In particular, in addition to cylindrically shaped LED radiance sources, flat panel or rectangular LED radiance sources can be constructed according to the present invention.

The LED radiance sources of the present invention are preferably designed to be compact and portable. Accordingly, the size of the LED arrays are typically minimized subject to ensuring that, for example in the case of a circular array arrangement, the spatially uniform radiance output along the central axis of the resulting LRS has a suitable diameter or width for a given application. Otherwise, the size of the LED arrays, and associate size of the LRS can be increased as desired.

According to one embodiment, which is discussed in detail below, the LED arrays are produced by fixing individual LEDs on a circuit board. In such an arrangement the overall size or compactability of the resulting LED array is physically limited by structure. Accordingly, it has been determined that a more compact LED array, and resulting LRS, can be produced by fabricating the LEDs direction on a substrate using chip-on-board technology. Such an arrangement would result in size reduction and greater radiance levels than can be achieved for example configuring typical 5 mm LED packages on a circuit board.

The LED arrays that are used in the LED radiance sources of the present invention are preferably provided as modules that are interchangeable. This will allow selection and change of LED arrays that have different center wavelengths. In the examples discussed below, LEDs having 395 nm, 660 nm and 990 nm wavelengths were tested in the LED radiance sources of the present invention. However, it is to be understood that LEDs of any conventional wavelength can be used in the LED radiance sources of the present invention.

Figure 2:
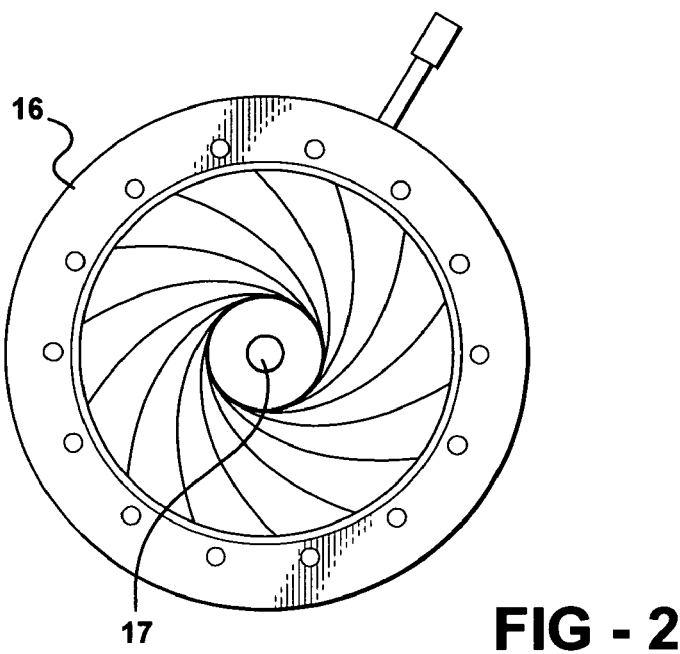
FIG. 2 is a planar end view of the LRS of FIG. 1.

FIG. 1 is a cross-sectional side view of a LED Radiance Source (LRS) according to one embodiment of the present invention. FIG. 2 is an end view of the LRS of FIG. 1. The LRS shown in FIGS. 1 and 2 includes a tubular housing 1 which can be made from any suitable strong material such as a metal. In one embodiment, the housing 1 was formed from a length of tubular aluminum that had a diameter of about 56 mm and a length of about 150-155 mm. The LED head 2 includes an LED array 3 and temperature control components described in more detail below. The LED head 2 is configured as a modular unit that can be replacably inserted into the rear end 4 of the housing 1 and secured therein by any suitable means such as a retaining ring (not shown) that can be threadedly received in the rear end 4 of the housing 1, or a snap-clip retaining ring that can engage within a groove provided within the rear end 4 of the housing 1, or any suitable cap, bayonet, lour lock, or other engaging structure/assembly, etc.

As shown in FIG. 1, the rear end 4 of the housing 1 has a stepped bore portion that provides an abutment 5 against which the LED head 2 can be position as shown (with a retaining ring on the other side). Also as shown in FIG. 1, the housing 1 includes a translucent lining 6 of polytetrafluoroethylene (PTFE) that extends from the abutment 5 (or LED head 2) forward and beyond the front end 7 of the housing 1.

In the embodiment of the LED radiance source depicted in FIGS. 1 and 2, the LED array 3 includes a plurality of LEDs that are mounted on a circuit board 8. According to one embodiment an LED array 3 was formed with thirty-six 5 mm diameter LEDs on a 50 mm diameter printed circuit board 8. In this embodiment the LED circuit was divided into four parallel sets of nine LEDs that were connected in series. Each of these nine LEDs was provided with a circuit-limiting resistor. In order to make the light projected from the LEDs more diffuse, the faces of the 5 mm LED packages were roughened.

Temperature control of the LEDs is accomplished by mounting a thermo-electric cooler (TEC) 9 on a cold plate 10 directly onto the soldered leads of the back side of the circuit board 8. Thermally conductive epoxy can be used to fill the air spaces between the surfaces. The cold plate 10 helps to evenly distribute the temperature across all the leads. A small thermistor is sandwiched between the cold plate 10, and the circuit board 8 and fixed in place by the thermally conductive epoxy. The thermistor allows for monitoring the temperature of the cold plate 10 and the thermoelectric cooler 9 allows for controlling the temperature of the cold plate 10. By controlling the temperature of the cold plate 10 the temperature of the LED head 2 can be controlled, thereby allowing for control and stabilization of temperature-dependent radiation output, i.e., radiance and wavelength stability. As shown in FIG. 1 a heat sink 12 can be provided behind the cold plate 10. According to another embodiment, a heat exchanger in which cooling fluid is circulated can be used in place of the thermoelectric cooler.

As shown in FIG. 1, a monitoring photodiode 13 is positioned perpendicular to the optical axis of the LED radiance source, approximately midway between the LED head 2 and a diffuser 14 that is positioned across the front end 7 of housing 1 as shown. A small hole 15 provided in the housing 1 beneath the photodiode 13 allows the photodiode 13 to view the opposite wall of the housing through the translucent polytetrafluoroethylene (PTFE) liner 6 in an overfilled mode. The photodiode 13 can comprise an unfiltered Si photodiode according to one embodiment of the present invention. In other embodiments, other detectors and narrow band filters can be used in place of the Si detector package. The photodiode 13 (or other detector) monitors radiance output of the LEDs. Monitored variations in radiance output can be used as feedback to control the current used to drive the LEDs, and/or the temperature of the LEDs it being noted that temperature and drive current can be independently controlled.

The LED radiance sources of the present invention can be operated in a constant-current mode. In order to avoid initial thermal variations and fluctuations, thermal steady state should be reached before use by allowing the LED radiance sources to warm up for an initial period of time. Alternatively, warm-up time can be decreased by setting the thermoelectric cooler 9 to a desired operating temperature and the signal from the monitor photodiode can be used to determine when the LED radiance sources have reached a stable operating state.

For use as a radiance source, a bare diffuser 14 can be mounted at the front end 7 of the housing 1 of the LED radiance sources as depicted in FIG. 1. The absolute radiance of the LED radiance sources can be determined, and then continuously monitored using the monitor photodiode 13. In order to minimize possible temperature-dependent spectral shifts, the temperature of the LED radiance sources can be set to the same constant temperature as measured during the radiometric calibration. Alternatively, temperature dependent variations in radiation output can be controlled by monitoring radiation output using the monitor photodiode 13 and using the resulting monitored signal as a feedback signal to control the current supplied to the LEDs.

For measurements of SSE, a diffuser with a central obscuration can be added with a variable-aperture iris 16 mounted immediately in front of the front end 7 of the LED radiance source as shown in FIG. 1. The diameter of the obscuration 17 can be determined based upon the spot size of the radiometer that is being characterized. Both sides of the iris 16 should be blackened to reduce reflections between the radiometer being tested and within the source. Small changes in the throughput of the source can be compensated for by normalizing the signal from the radiometer with the monitor photodiode signal. Also shown in FIG. 1 is a mounting structure 18 that supports the LED radiance source. The illustrated mounting structure 18 includes a ring mount 19; however, it is understood that any convenient mounting structure can be used.

Radiance measurements of an LED radiance source built in accordance to the present invention were determined as follows. The spectral radiance of the LED radiation source was determined with 395 nm, 660 nm and 950 nm LED modules having a ground glass diffuser by comparison to a calibrated tungsten-strip lamp using a spectroradiometer. The entrance to the spectroradiometer was masked to view a 0.6 mm by 0.8 mm area at the center of the front diffuser of the LED radiance source for comparison with the tungsten-strip lamp. The aperture stop of the spectroradiometer was limited to f/8 by f/16. The results of the spectral radiance measurements are shown in FIG. 3.

Figure 3:
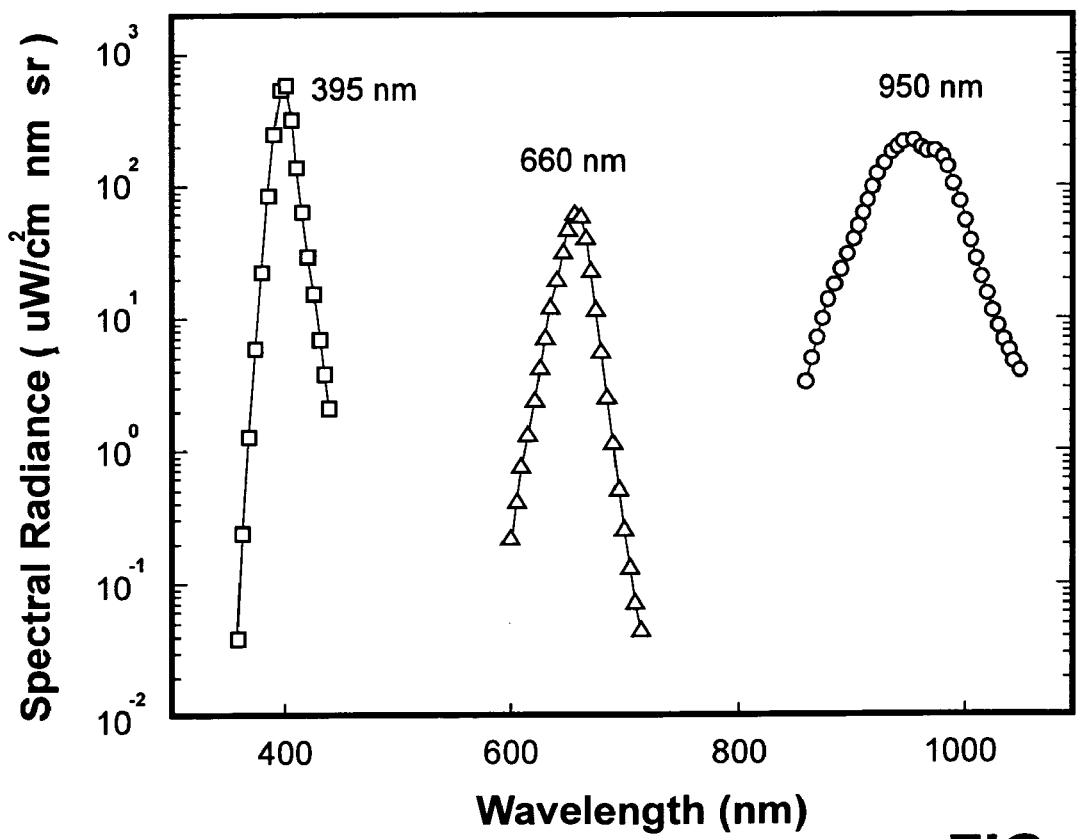
FIG. 3 is plot of spectral radiance ($\mu W/cm^2$ nm sr) verses wavelength (nm) (measured in 5 nm increments).

FIG. 3 is a plot of spectral radiance ($\mu W/cm^2$ nm sr) verses wavelength (ram) (measured in 5 nm increments). As shown in FIG. 3 each of the 395 nm, 660 nm and 950 nm LED modules emitted a relatively narrow band of radiation with an identifiable peak wavelength.

The spectral radiance of the LED modules was measured and the radiance temperature of the 395 nm, 660 nm and 950 nm LED modules were determined to be 2491° K, 1521° K and 1125° K, respectively. The measured spectral widths of the LRS radiances are wider than the spectral widths of the individual LEDs due to the wavelength variation of the individual LEDs in the thirty-six LED modules.

Measurements of the aging, temperature dependence and relative spectral distribution were made of the individual LEDs of an LED head/array in a temperature-controlled light-tight box. A rotation stage with sixteen positions was oriented to project the light of individual ones of the LEDs of an LED head/array under test into an optical fiber that was coupled to a spectrograph. Aging measurements were made of both 395 nm and the 660 nm LEDs over a period of several hundred hours. After one hundred hours, the 660 LEDs showed a 10% decrease in radiance while the 395 nm LEDs showed a 35% decrease in radiance over the same period of time. Both LEDs showed signs of stabilizing.

Radiance measurements were repeated while temperature of the LEDs was varied from 20° C. to 30° C. The radiant intensity of the 660 nm LEDs was found to decrease by 5% with a 10° C. increase in temperature as measured over the range of from 20° C. to 30° C. The radiant intensity of the 395 nm LEDs decreased by 3% with a 10° C. increase in temperature as measured over the range of from 20° C. to 30° C. The center wavelength of the 660 nm LEDs was found to shift to longer wavelengths by 1.5 nm for a 10° C. increase in temperature over the range of from 20° C. to 30° C., while the 395 nm LEDs shifted to longer wavelengths by 0.4 nm for a 10° C. increase in temperature over the range of from 20° C. to 30° C.

Figure 4:
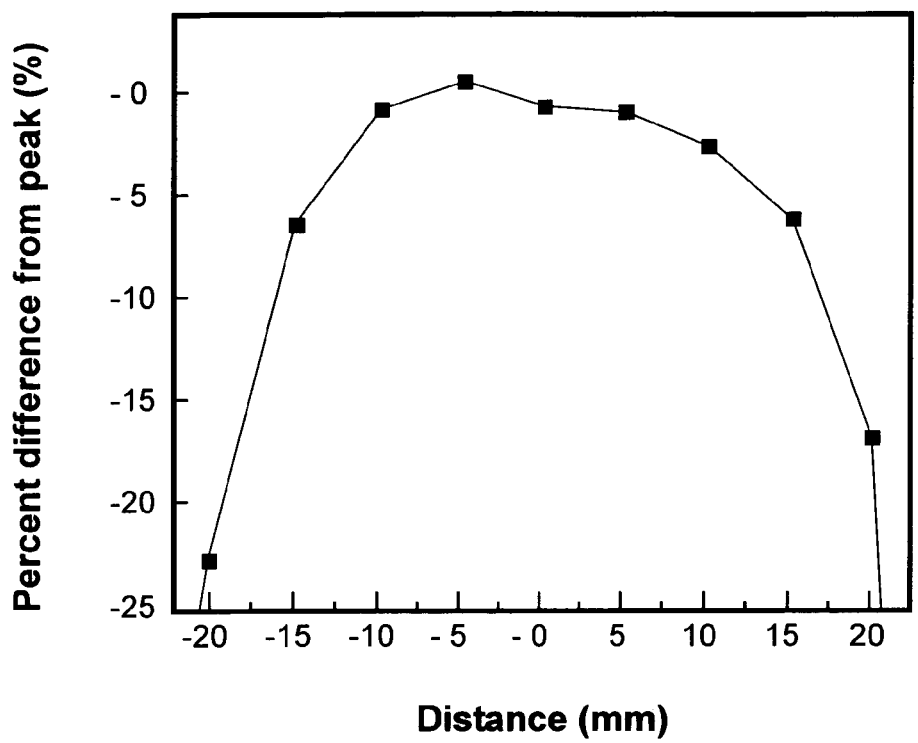
FIG. 4 is plot of the percentage difference from peak value verses distance (mm) from the axial center of the LED radiance source.

Measurements of the spatial uniformity of the radiance produced by the LED heads/arrays were made using a radiometer with an f/12 geometry and a target size of 1 mm diameter. The spatial scans were made in 5 mm increments across the front of the LED radiance source. FIG. 4 is a plot of the percentage difference from peak value verses distance (mm) from the axial center of the LED radiance source.

As shown in FIG. 4, the radiance is relatively spatially uniform over a large portion of the central of the output. The drop-off in the signals near the edge of the LED radiance source is due to a fall off in the irradiance from the edge of the LED circuit board. The LED radiance source was found to be uniform to less than 3% in the central 25 mm. A more uniform source could be achieved by simply using a larger LED array at the rear of the LED radiance source.

Figure 5:
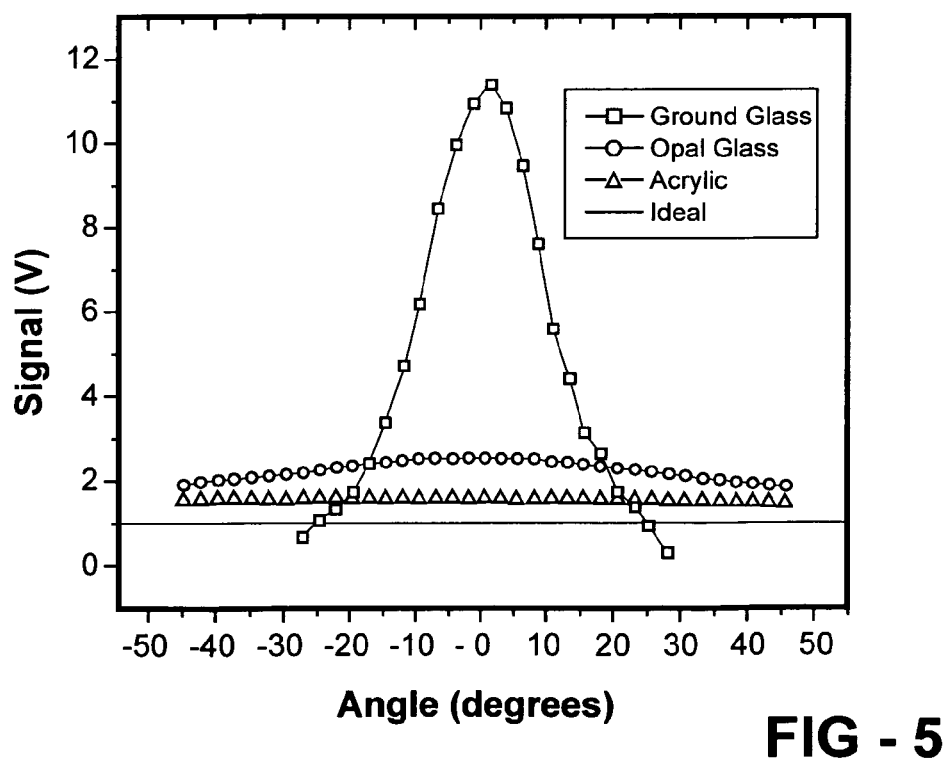
FIG. 5 is a plot that shows the angular distribution of different types of diffusers.

Angular uniformity of the radiance output was measured as follows. The LED radiance source was mounted on a rotation stage so that the axis of rotation was about the center face of the front diffuser. The measurements were performed with the f/12 imaging radiometer with a target size of 1 mm diameter at the center of the front diffuser. Measurements were made at every 2.5° from ±45° or until the signal dropped by more than 95% of its peak value. The measurements of angular uniformity are plotted in FIG. 5 for ground glass, flashed opal diffusers and an acrylic volume diffuser. The ideal lambertain source is plotted as a straight line. The differences in the y-axis are due to the different transmissions of the respective materials. The choice of diffuser depends on the type of instrument being characterized. Although the acrylic volume diffuser has transmission closest to that of a lambertain source, the use of the acrylic volume diffuser results in a factor of 10 reduction in the transmission. Since the ground-glass diffuser is not lambertain over a small angular acceptance as found for radiometers with f/10 corresponding to ±2.9°, these deviations from a lambertain source can be accepted in order to obtain the increased transmission of the ground-glass diffuser.

Temporal stability of the 660 nm LED was determined using the monitor photodiode. After an initial burn-in of more than two hundred hours, the signal was monitored over periods of ten hours. The deviation from the mean was less than 0.1% over that period of time. This measurement is in agreement with previous studies of LED source stability.

During the course of the present invention, a portable LED radiance source was developed for the purpose of characterizing optical pyrometers. The radiance source was 90 mm in diameter by 185 mm in length. The selection of different wavelengths was made by replacing interchangeable LED modules. The LED modules were built using 395 nm, 660 nm and 990 nm center wavelength LEDs. The 660 nm module with a full-width-half-max (FWHM) of 20 nm provides an effective source for characterizing radiation thermometers with center wavelengths at 650 nm. The 660 nm LRS was found to be lambertian over a ±20 degree full angle when used with an acrylic volume diffuser and had a uniform radiance to within 2.5% over the central 25 mm. A monitor photodiode was used to monitor the stability of the LEDs.

Compact, temporally stable and lambertain radiance sources can be developed with the use of LEDs according to the present invention. As discussed above, a monitor photodiode provided in the LED radiance sources can be used for feedback control of the LED radiance sources, resulting in much better temporal stability than a current-stabilized system. Due to the ever-increasing number and variety of LEDs, the possibility exists to develop many different inexpensive and reliable sources depending on the center wavelength of interest. The LED radiance sources of the present invention are especially useful for the ultraviolet and blue wavelength regions where tungsten-halogen lamp instrumented integrating sphere sources do not have sufficient outputs due to the spectral shape of the lamps.

The ability to select and change the spectral peak of the LED radiance sources of the present invention provides for application specific functionality. For example, in ocean color remote sensing, currently used calibration sources, such as incandescent lamps, peak around 950 nm. In contrast, the water-leaving radiance in the open ocean is blue, peaking at 450 nm. A calibration source with a relative spectral peak similar to the measured ocean color radiance would reduce sources of systematic error in ocean color measurements arising from stray light or wavelength errors in the instruments.

An ultraviolet radiation thermometer centered at 395 nm for the measurements of the detector-based temperatures of the metal-carbon eutectics is possible using the concepts of the present invention. This center wavelength will reduce the temperature uncertainties from the radiance responsivity uncertainties. Since the scattering of materials is wavelength dependent, the uncertainties due to the SSE can be assessed using a LED radiance source according to the present invention which is centered at 395 nm. Many types of glass also show fluorescence with incident ultraviolet radiation and thus, by using a 395 nm LED radiance source according to the present invention, the lens properties can be determined.

Since the LED radiance sources tested during the course of the present invention were found to be spatially uniform only near the center, different designs and configurations of the LED modules (than discussed in reference to FIG. 1) can be considered in order to increase the spatial uniformity. Fabricating LEDs in high density configurations using chip-on-board technologies will allow much greater radiance levels than can be achieved using typical 5 mm LED heads/arrays. Densities of up to 300 LED chips can be placed with a 50 mm diameter circle. Increasing the density inherently increases the spatial uniformity over the LED array. Achieving higher radiance levels also allows the design to incorporate more optics such as several diffusers to further improve the spatial uniformity. Another advantage of using chip-on-board fabrication technologies is the ability to influence the junction temperature of the LEDs. Typical 5 mm LEDs are encapsulated in epoxy and the encapsulation thermally isolates the LEDs and hinders the ability to control the junction temperature. Chip-on-board technologies allow the LED chips to be placed directly on a ceramic substrate with high thermal conductivity. Maintaining a lower junction temperature may also enhance the long-term stability.

As noted above, the LED illuminated radiance sources of the present invention are useful for the calibration and characterization of radiation thermometers, night vision devices, environmental remote sensing systems, biological agent detection, and any radiometer which needs a stable radiance source. Other applications include remote sensing for satellite calibration and/or validation, a uniform UV source for biological markers and fluorescent markers, check source for Fourier Transform Infrared Spectroscopy (FTIR), a resolution target (such as a USAF target, etc.

Although the present invention has been described with reference to particular means, materials and embodiments from the foregoing description, one skilled in the art can easily ascertain the essential characteristics of the present invention and various changes and modifications can be made to adapt the various uses and characteristics without departing from the spirit and scope of the present invention as described above and from the scope of the claims that are attached.

What is claimed is:

1. A method of providing a stable, uniform source of radiation which comprises the steps of: a) providing an array of a plurality of LEDs, each one of the plurality of LEDs of the array having a common center wavelength; b) supplying current to the plurality of LEDs to cause the plurality of LEDs to emit radiation; c) monitoring the radiation emitted from the plurality of LEDs; and d) using the monitored radiation in step c) to control at least one of the temperature of the plurality of LEDs and the current supplied to the plurality of LEDs and further comprises the step of providing the radiation as a calibration or reference source for at least one of a radiation thermometer, night vision device, environmental remote sensing system, and biological agent detection system.

* * * * *